United States Patent [19]

DeCote, Jr.

[11] Patent Number: 4,768,511
[45] Date of Patent: Sep. 6, 1988

[54] AUTOMATIC SENSITIVITY CONTROL FOR IMPLANTABLE CARDIAC PACEMAKERS

[75] Inventor: Robert DeCote, Jr., Miami, Fla.

[73] Assignee: Telectronics N.V., Netherlands Antilles

[21] Appl. No.: 884,014

[22] Filed: Jul. 10, 1986

[51] Int. Cl.$^4$ .............................................. A61M 1/36
[52] U.S. Cl. .......................... 128/419 PG; 128/419 P
[58] Field of Search .................. 128/419 PT, 419 PG, 128/696, 708

[56] References Cited

U.S. PATENT DOCUMENTS

| | | | |
|---|---|---|---|
| 4,240,442 | 12/1980 | Andresen et al. | 128/708 |
| 4,325,384 | 4/1982 | Blaser et al. | 128/696 |
| 4,513,752 | 4/1985 | Weyant | 128/696 |
| 4,585,001 | 4/1986 | Belt | 128/708 |
| 4,677,986 | 7/1987 | DeCote, Jr. | 128/697 |

Primary Examiner—William E. Kamm
Assistant Examiner—Timothy J. Keegan
Attorney, Agent, or Firm—George H. Gerstman

[57] ABSTRACT

A cardiac pacer is described which includes a pulse generator for providing pacing pulses and an electrical lead for bilateral (or bidirectional) (i.e., sense and pace) connection to a chamber of the heart. A fixed gain, tuned sensing amplifier senses selected activity of the heart chamber. The output of the sensing amplifier is connected to a pair of voltage comparators. One of the voltage comparators has a slightly lower threshold and thus a slightly higher sensitivity level than the other voltage comparator. Under closed loop control, the thresholds of the respective voltage comparators are automatically adjusted so that one of the voltage comparators will sense the selected activity of the heart chamber and the other voltage comparator will not sense the selected activity.

15 Claims, 4 Drawing Sheets

AUTOMATIC SENSITIVITY CONTROL FOR IMPLANTABLE CARDIAC PACEMAKERS

CROSS-REFERENCE TO RELATED APPLICATIONS

This application is related to application Ser. No. 874,444, filed June 16, 1986, and application Ser. No. 870,398, filed June 4, 1986.

FIELD OF THE INVENTION

This invention concerns a novel automatic sensitivity control for implanted cardiac pacemakers.

BACKGROUND OF THE INVENTION

Cardiac pacing systems include a cardiac pacer connected to a lead which conducts stimuli from the pacer to an electrode implanted either on the surface of or within the cardiac chambers. Certain cardiac pacers, including those designated VOO pacers, emit stimuli at a predetermined rate, in pulses per minute. However, there are certain other models, including those designated VVI pacers, in which the output pulse is suppressed in the presence of naturally occurring cardiac electrical activity. Such models detect cardiac electrical activity via the lead during a portion of the interval termed the alert period between output pulses. When such activity is detected during the appropriate portion of the pulse to pulse interval, a new timing cycle is initiated with time zero of the new interval being the time of detection of the electrical activity. Such electrical activity detected in, e.g., the ventrical, may be that which normally occurs from the atrium to the ventricle or may be due to a premature ventricular or atrial contraction dependent upon the lead placement and pacer type.

Such cardiac pacers which detect electrical activity during the alert period must have a sensitivity threshold for enabling such detection. The sensitivity of a cardiac pacer is generally considered to be that level, in millivolts, which the electrical activity resulting from the depolarization of the cardiac muscle must exceed within a given time period for the cardiac depolarization to be detected by the sensing amplifier of the cardiac pacer. For example, if the sensitivity of a cardiac pacer has been set at one millivolt, then the cardiac electrical depolarization must obtain the one millivolt level within, for example, a 30 milliseconds time period to be detected by the cardiac pacer, thereby inhibiting the output stimulus and resetting the timing cycle of the cardiac pacer.

The sensitivity of these "sensing" cardiac pacers may be preset during manufacture. In other models of sensing cardiac pacers, the sensitivity may be externally programmed to various levels. Such externally programmed changes in sensitivity are accomplished by the use of an external device and usually require a visit to the physician's office. Therefore, there is no automatic change in sensitivity levels if spontaneous myocardial electrical activity ceases to be detected by the implanted cardiac pacer.

The importance of proper sensitivity adjustment cannot be overemphasized. If the sense amplifier of the pacer is not sensitive enough, proper sensing of cardiac activity will not occur. On the other hand, if the sense amplifier is too sensitive, it may sense noise and/or myopotentials. Although a physician may be able to readjust for proper sensitivity of the pacer, many patients are unable to see their physicians often. Thus although the sense amplifier of a pacer is presumably programmed correctly at a particular time, the cardiac coupling parameters may change at a subsequent period of time (as in fibrotic tissue growth) and the sensitivity of the sense amplifier may consequently become either too low or too high.

The present invention obviates the need for a number of tuned amplifiers on a signal channel, and also obviates the need for utilizing a tuned amplifier in which the gain must be varied. In a system requiring the varying of the gain of a tuned amplifier, in addition to requiring many components there may be band pass detuning problems. Further, systems requiring multiple amplifiers or gain varying circuitry may suffer from lack of resolution because circuitry tends to become unwieldy for six or more sensitivity levels.

Therefore, it is an object of the present invention to provide a cardiac pacer in which sensitivity is automatically adjusted as required to optimally sense spontaneous cardiac electrical activity without requiring unwieldy circuitry.

Another object of the present invention is to provide an automatic sensitivity adjusting cardiac pacer in which a single fixed gain, tuned amplifier may be utilized. This may result in comparatively fewer components and the circuit of the present invention enables a resolution of greater than 250 sensitivity levels when an eight bit system is used. Instead of varying sense amplifier gain, the DC reference voltage at the inputs to a pair of sense detection comparators may be programmed and these DC levels may be under the direct software control of an N-bit digital to analog converter.

Other objects and advantages of the present invention may become apparent as the description proceeds.

SUMMARY OF THE INVENTION

In accordance with the present invention, a cardiac pacer is provided which includes a pulse generator for providing pacing pulses and an electrical lead for connection to a chamber of the heart. In the illustrative embodiment, a fixed gain sensing amplifier is provided for sensing selected activity of the heart chamber.

The electrical lead of the cardiac pacer is connected to the fixed gain sensing amplifier. The output of the fixed gain sensing amplifier is coupled to a pair of voltage comparators. One of the voltage comparators has a slightly lower threshold and thus a slightly higher sensitivity than the other voltage comparator. The thresholds of the respective voltage comparators are both simultaneously adjusted so that one voltage comparator will sense the selected activity of the heart chamber while the other voltage comparator will not sense the selected activity of the heart chamber that has been amplified by the sensing amplifier.

In the illustrative embodiment, each of the voltage comparators is internally identical and comprises an analog comparator having a positive input and a negative input. The coupling means comprises a precision signal rectifier having an output that is the absolute value of its input. The rectifier output is coupled directly to the positive input of both voltage comparators.

In the illustrative embodiment, the self-adjusting means includes means for providing sensing threshold levels to the negative comparator inputs which are controlled so that (a) if neither voltage comparator senses the selected activity the thresholds of both voltage comparators are decreased, (b) if one voltage comparator senses the selected activity but the other voltage comparator does not sense the selected activity, the threshold levels are unchanged, and (c) if both voltage comparators sense the selected activity the thresholds of both voltage comparators are increased.

In the illustrative embodiment, the sensing threshold level adjusting means comprises a digital to analog converter. A microprocessor provides digital signals to the digital to analog converter's input and there is a resistive scaling circuit coupled from the output of the digital to analog converter to the negative inputs of the voltage comparators for providing different voltage levels to the two negative inputs. The outputs of both voltage comparators are connected to inputs of the microprocessor.

A more detailed explanation of the invention is provided in the following description and claims, and is illustrated in the accompanying drawings.

DETAILED DESCRIPTION OF THE ILLUSTRATIVE EMBODIMENT

Figure 1:
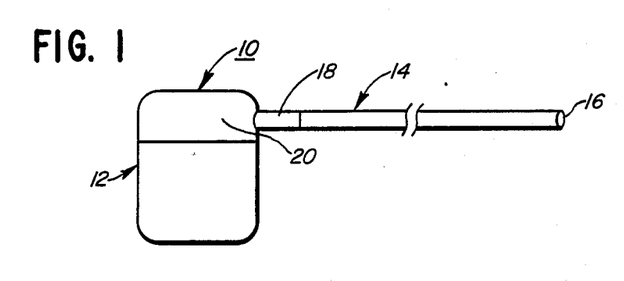
FIG. 1 is an elevational view of a cardiac pacing system in accordance with the present invention.

Referring to FIG. 1, there is shown an implantable cardiac pacing system 10 comprised of a pacer 12 and its pervenous lead 14. The lead 14 has at its distal end an electrode 16 which is electronically bonded to a helically coiled conductor wire. At the proximal end of the lead 14, the conductor wire is bonded to a lead terminal assembly 18 which is contained within the neck 20 of the implantable cardiac pacer 12. The lead terminal assembly 18 is in contact with the circuitry contained within the implantable cardiac pacer. The helically coiled conductor wires are contained within an insulating sheath generally of silastic or polyurethane.

Although this (or the foregoing) description pertains to a unipolar lead and a ventricular sensing pacer, the circuitry and operation described herein can be utilized in a dual chambered pacer, an atrial sensing pacer or a ventricular sensing pacer with either a unipolar or bipolar lead configuration.

Figure 2A:
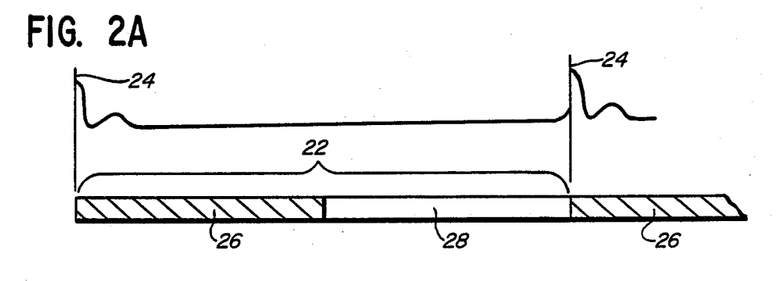
FIG. 2A is a diagram of a timing cycle occurring during stimulation.
Figure 2B:
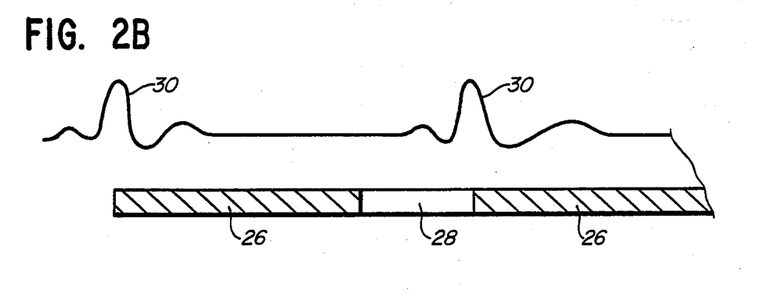
FIG. 2B is a diagram of the timing cycle of FIG. 2A that has been reset by an actually occurring ventricular activity.

Referring to FIGS. 2A and 2B, ventricular sensing pacer 12 is designed so that the interval between two stimuli 24 is divided into two periods, a refractory period 26 and an alert period 28. Either the emission of a stimulus pulse 24 (FIG. 2A) or detection of spontaneous electrical activity 30 (FIG. 2B) initiates a new refractory period 26 which is generally referred to as a new pacer cycle. Detection of spontaneous electrical activity 30 during the alert period 28, terminates and thereby shortens the alert period 28 (FIG. 2B).

The stimulus pulse 24 is transmitted from the implantable cardiac pacer 12 to the ventricle via the helical conductor wire within the insulation of the lead 14 through the distal electrode 16. Similarly, spontaneous ventricular electrical activity falling within the alert period 28 of the pulse to pulse interval 22 is sensed via the distal electrode 16 and transmitted to the ventricular sensing amplifier within cardiac pacer 12.

Figure 3:
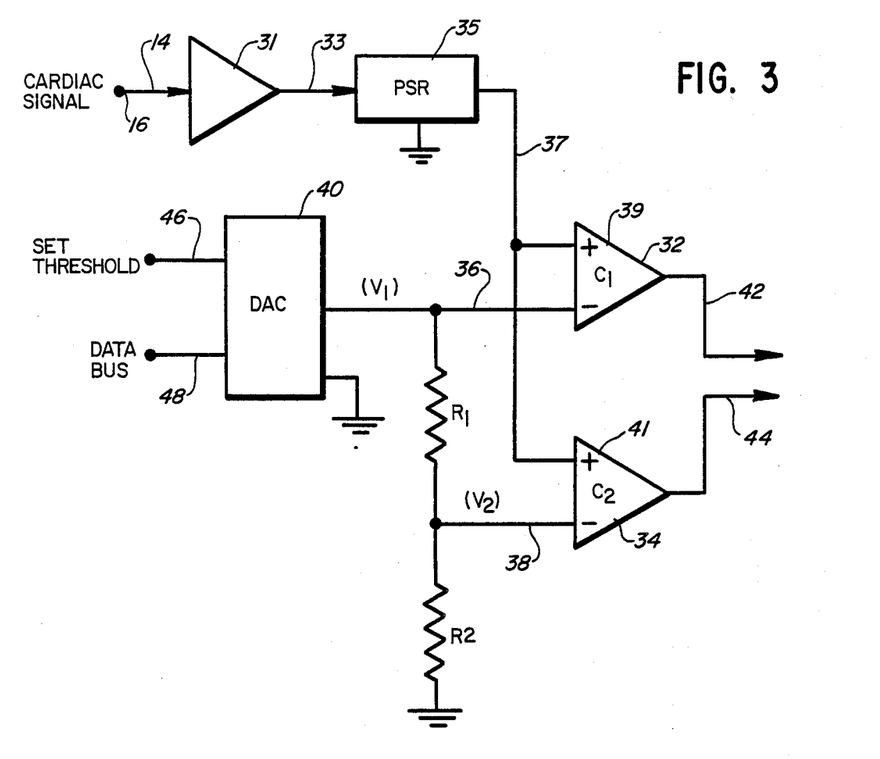
FIG. 3 is a block diagram of a sensing circuit used in the cardiac pacing system of the present invention.

Referring to FIG. 3, the system of the present invention includes a sensing amplifier 31 of conventional design with a fixed gain and passband. The output of the sense amplifier 31 is fed via line 33 to a precision signal rectifier (PSR) 35, the output of which is the absolute value of its input. The all positive output of precision signal rectifier 35 is fed via line 37 into positive inputs 39 and 41 of two analog voltage comparators 32 and 34, respectively. The negative inputs of voltage comparators 32 and 34 are connected via lines 36 and 38 to the output of a digital to analog converter 40 (DAC). The negative input of voltage comparator 32 receives the full DC output voltage ($V_1$) of the N-bit digital to analog converter 40 while the negative input of comparator 34 receives the reduced voltage from the output of a resistive scaling circuit comprising resistors R1 and R2 having an output $V_2$ which is analytically equal to $V_1$ R2/(R1+R2).

The outputs of comparators 32 and 34 are connected via lines 42 and 44 to two inputs of a microprocessor, a control output of which is connected to DAC input 46 and whose data bus 48 controls the output voltage level of N-bit digital to analog converter 40.

In operation, the patient's cardiac activity is coupled from the electrode 16 (FIG. 1) through the lead 14, and to the circuitry within the pulse generator 12. The cardiac electrical activity signals are fed into sense amplifier 31 (FIG. 3). Sense amplifier 31 may be single ended or differential. The passband of the amplifier 31 is designed to selectively amplify cardiac signals while suppressing myopotentials and other undesired signals. The amplified cardiac signal is converted to an absolute value signal by precision signal rectifier 35.

Figure 4:
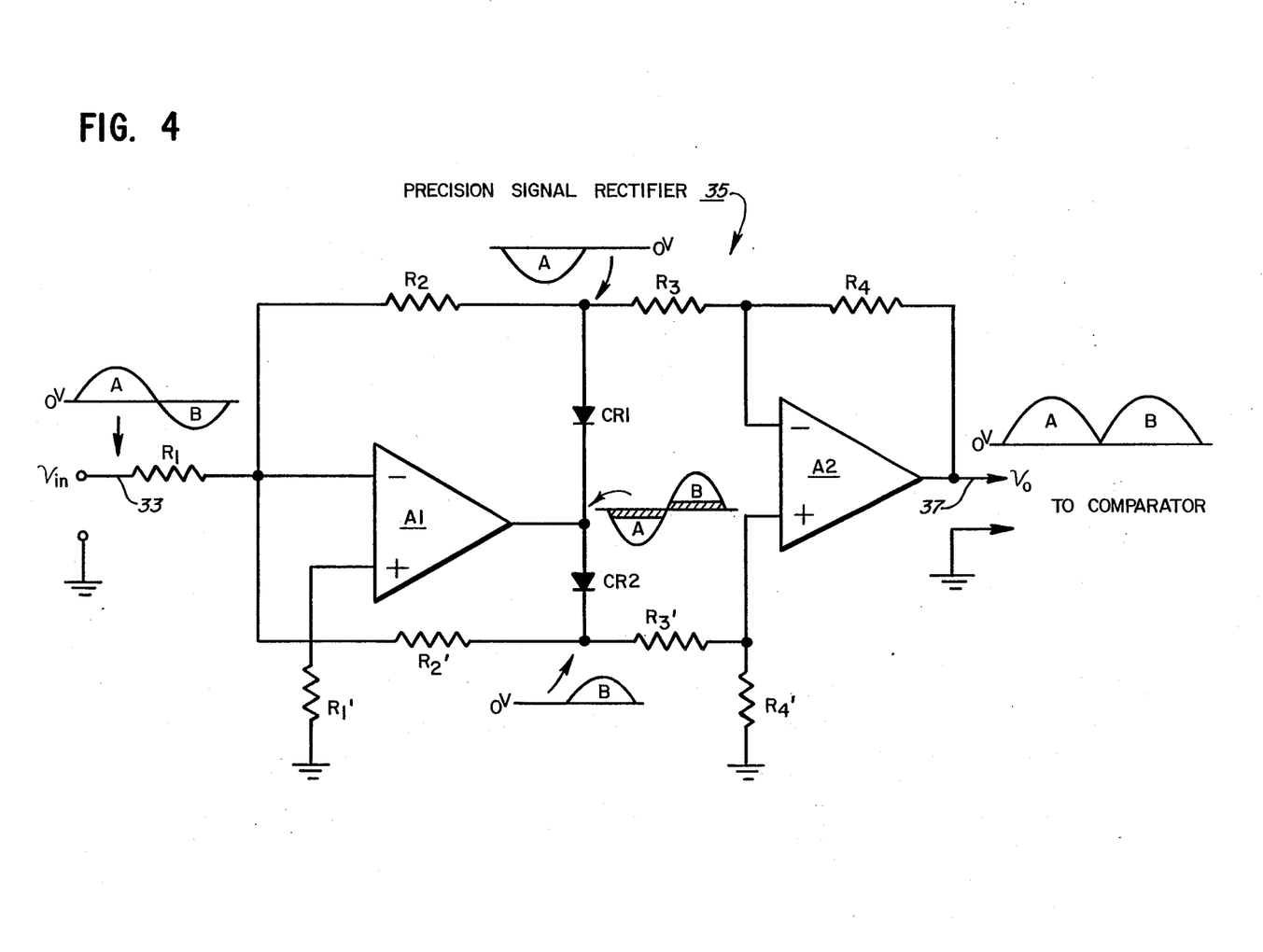
FIG. 4 is a schematic diagram of a precision signal rectifier used in the cardiac pacing system of the present invention.

Referring to the PSR schematic shown in FIG. 4, all resistors are precision matched; i.e., R1=R1', R2=R2', etc. Operational amplifier A1 is configured as an inverting amplifier, but with two distinct negative feedback paths; one for feedback current due to negative output voltage (through CR1 and R2) and another for feedback current due to positive output voltage (through CR2 and R2'). Assume a balanced sinusoidal voltage is applied to the input with lobes A and B, as shown. Thus lobe-A, which comes in positive-going, is inverted by A1's action and will appear across R2 because CR1 allows conduction in that direction. Meanwhile, CR2 is back-biased, so R2' is at 0 Volts. A little later, with negative lobe-B at the input, A1 still inverts, so a positive lobe will now appear at A1's output. This means CR2 conducts, and positive lobe-B appears across R2', as shown.

The voltage drops across the diodes are of no consequence because feedback current is determined solely by input current (Iin=Vin/R1). Thus, in the unity gain case (R1=R2=R1'=R2'), A1's output is not simply an inverted version of the input, but includes baseline offset voltages equal to the diode's forward conduction drops. This is of no consequence in the given configuration because A1's output is not used directly. A1 merely provides whatever voltage is required to obtain feedback currents through R2 or R2' which are always instantaneously equal to Vin/R1.

Operational amplifier A2 is configured as a difference amplifier. Therefore, negative-going lobe-A, which is fed to its inverting side at R3, appears positive at A2's output. And correspondingly, positive-going lobe-B, which is fed to its non-inverting side at R3', also appears positive at A2's output. Thus, the combined signal splitting action of A1, and the differential amplifier action of A2 produces a precision rectified version of Vin at A2's output. As indicated, this rectified signal is fed via line 37 to the positive inputs of both comparators 32 and 34.

Figure 5:
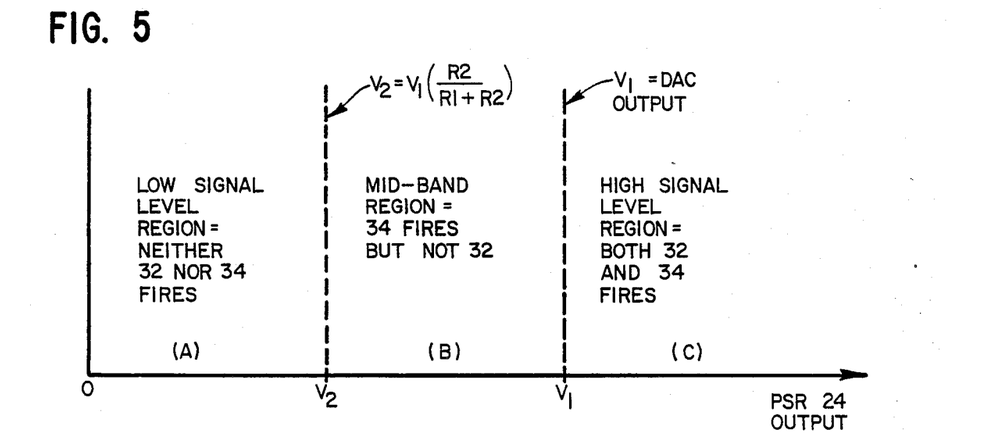
FIG. 5 is a diagram showing the three levels of operation of the sensing circuit of the present invention.

For any given DAC output there are three regions of comparator operation as illustrated in FIG. 5. At the low signal level, region (A), neither comparator 32 nor 34 detects the cardiac signal. In the mid band region (B), comparator 34 detects the cardiac signal but comparator 32 does not detect it. This is the ideal region of operation. At the high signal level region (C) both comparators 32 and 34 detect the incoming cardiac signal.

For illustrative purposes, it will be assumed that the voltage reduction scaling factor afforded by R1 and R2 is 0.8 so that the threshold of comparator 32 (V1) is always 25 percent higher than the threshold of comparator 34 (V2). In this instance, we can say that the threshold of comparator 34 (V2) is X millivolts while that of comparator 32 (V1) is 1.25 X millivolts, referred to input. As a first example, consider that all signals are below the V2 threshold of X millivolts. Neither comparator 32 nor comparator 34 will fire. This is region (A) in FIG. 5. Here either the V2 threshold value has been set too high to detect the patient's cardiac activity or no spontaneous cardiac activity has occurred because the patient's intrinsic rate is below that of the programmed rate of the cardiac pacer 12. After a preprogrammed "no comparator action detected" interval, the microprocessor causes the pacing circuit to emit a stimulating pulse to the cardiac chamber. After one or more such consecutive pacing cycles, the microprocessor adjusts the output of the digital to analog converter 40 to a preprogrammed lower threshold level. There are two principal Region-A response techniques (algorithms) for lowering the threshold levels, as follows: (1) Reduce the sensing threshold levels (DAC output) in a series of steps of predetermined step size (either NmV or N % per pacer cycle) until either comparator 34 starts sensing, or a maximum predefined sensitivity (minimum threshold level) is attained. This is the preferred sensitivity increase algorithm, but relative programming complexity (hence, memory space requirements) may make it less desirable than the following approach. (2) Reduce the sense threshold level to the lowest predefined value in one "giant" step. This response algorithm has the advantage of being much simpler, but is relatively crude. As a consequence, a response of this type is more likely to result in the sense amplifier temporarily sensing noise and/or myopotentials.

In the second scenario, comparator 34 fires and comparator 32 does not fire. This is region (B) in FIG. 5 and is the desired modality of operation as the amplitudes of the patient's electrical activity lie within the window between the thresholds of comparator 34 (V2) and comparator 32 (V1). In this case, no change is made in the threshold values of the digital to analog converter 40. Upon sensing of the cardiac signal, the microprocessor causes the timing cycle to reset and the stimulation pulse is inhibited.

As a special case, consider a situation where only comparator 34 is firing but the system is detecting too many events per unit time, we interpret this as "noisy" sensing. In such a case, the microprocessor will increase the output voltage of the digital to analog converter 40 so that the threshold of the comparator 34 (V2) will be raised above the noise background but will still sense the slower cardiac signals. If noise is detected up to the highest threshold, at which comparator 34 still senses, the effective noise level is equal to or greater than the peak value of the cardiac signal. In such instances, the threshold level will be maintained near the top of the noise peak, and the pacer will pace at the programmed rate. This is called noise rate pacing. When the noise subsides, the system will automatically respond to the incoming cardiac signals as discussed herein. On the other hand, if comparator 34 began by detecting noise signals and the threshold was automatically increased to be above the noise, then this would represent an optimum utilization of the present invention by providing a self-adapting noise immunity capability.

In the third scenario, both comparators 32 and 34 detect incoming signals and fire. This is region (C) in FIG. 5. The microprocessor acts to increase the output voltage of the digital to analog converter 40. If rapid, noise-type sensing is detected, the rate of threshold voltage increase can be higher than if noise is not detected. This cyclical sensing in both comparators is repeated until region (B) sensing is attained. In the event that both comparators 32 and 34 continue to detect incoming signals and the digital to analog converter 40 output voltage has been increased to its maximum value, the system is responding to inordinately large but real signals in a systematic manner, i.e., either normal sensing or noise rate sensing will obtain, as is appropriate. In either case, the maximum threshold (minimum sensitivity) is the optimal pacer response.

It is also possible to design this circuitry using a "cross-crossed" control configuration. Referring to FIG. 3, the full output of the DAC 40 can be tied directly to the two negative comparator inputs, and the full PSR output on line 37 connects to the top of the attenuator (R1/R2) and the positive input 41 of comparator 34 (only), whereas an attenuated version of the PSR output (from the junction of R1/R2) goes to the positive input 39 of comparator 32 (only). Thus, instead of attenuating the threshold, the output of the PSR 35 is attenuated. The given comparator assignment simply keeps comparator 34 more sensitive than 32.

Figure 6:
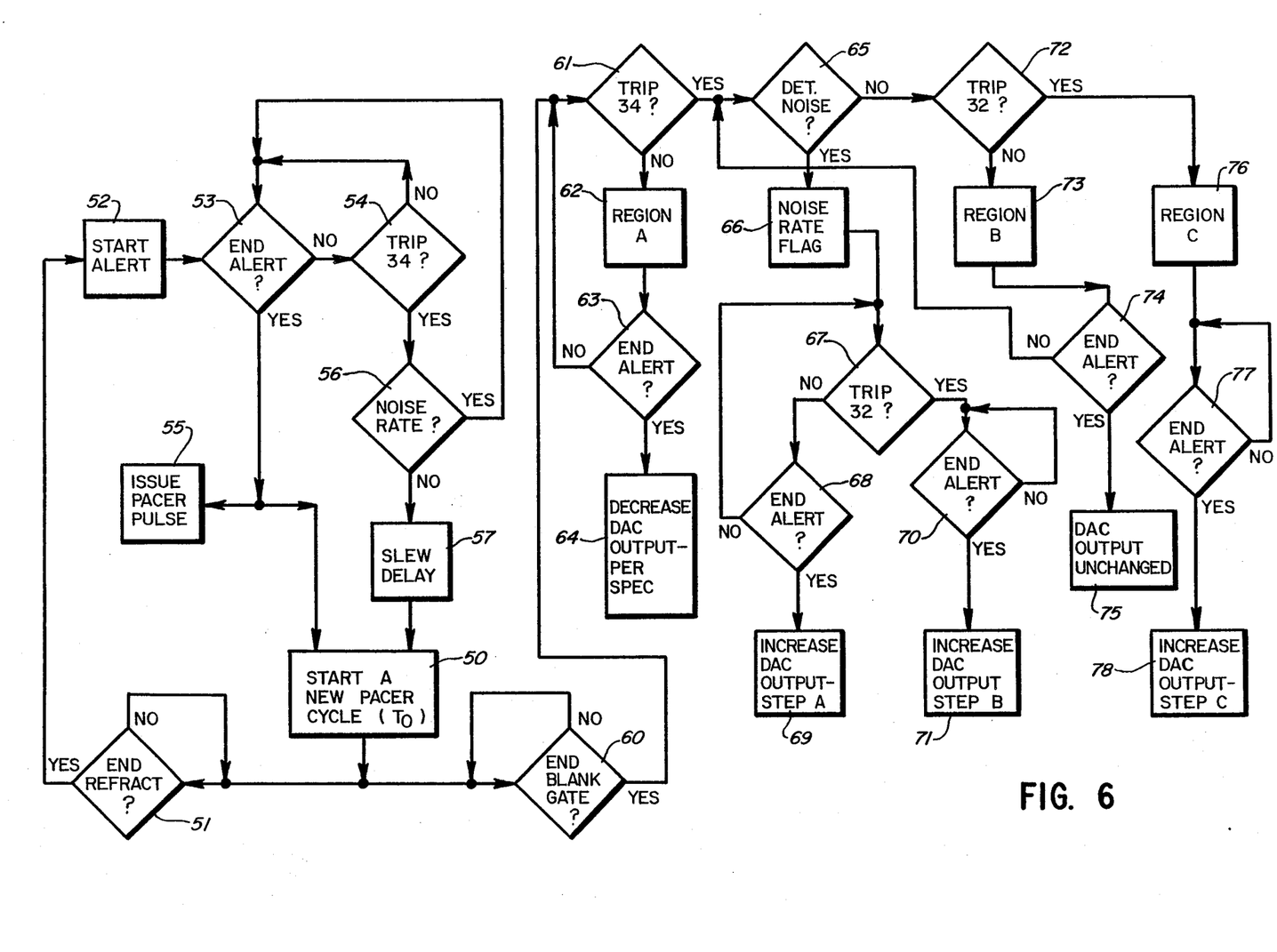
FIG. 6 is a flow chart of one embodiment of the cardiac pacing system of the present invention.

Taking an overview of the flow chart in FIG. 6, the pacing function is contained in the loop at the far left (blocks 50 to 57), whereas the sensing function extends through all the generally vertical branches on the right side of the diagram (blocks 60 to 78).

The discussion of the pacing function begins at block 50; START A NEW PACER CYCLE (To). As indicated, this event initiates two timing functions—refractory 51 and blanking 60. Blanking is a sensing related function, and is discussed below. As indicated by block 51, during the relatively long refractory interval, no pacing loop activity takes place. When refractory ends, pass through START ALERT 52, and immediately enter the END ALERT? interval 53, the end of which, in turn, starts a new pacer cycle. The alert interval can terminate (to block 50) in any one of three ways, as follows:

(1) The most sensitive comparator does not sense cardiac activity (TRIP 34?, 54 is a NO), and END ALERT? 53 simply times out, in which case ISSUE A PACER PULSE, 55, and simultaneously START A NEW PACER CYCLE (To) per block 50. This constitutes a patient support pacer cycle; the patient's heart was stimulated at the programmed rate.

(2) TRIP 34?, 54 is a YES and NOISE RATE? 56 (which examines the NOISE RATE FLAG, block 66) is a NO. This corresponds to a "noise-free" sensed cardiac activity cycle. In this case introduce a small SLEW DELAY, 57, for sensing purposes (as discussed below), and START A NEW PACER CYCLE (To), 50, without issuing a pacer pulse; i.e., bypassing block 55. This constitutes a cardiac-inhibited pacer cycle. The rationale here is that sensing indicated that the patient did not need to be paced.

(3) The last pacer loop possibility is when TRIP 34? (block 54) and NOISE RATE? (block 56) are both YES. This corresponds to a noise detected cycle, in which case wait until END ALERT? 53 times out and ISSUE A PACER PULSE 55 just as if sensing had not occurred. This constitutes a paced noise-rate pacer cycle. The rationale here is that in the presence of noise, it is better to err on the conservative side, and assume the patient needs to be paced at the programmed rate.

Now turn to the sensing side of FIG. 6. Each new pacer cycle initiates a blank gate timing interval (block 60), during which time sensing cannot take place. Blanking is required to allow the relatively high pacer pulse energy to subside below the level at which it interferes with sensing. It is a much shorter interval than refractory (which, incidentally, is aimed primarily at preventing T-wave sensing). In general, immediately at the end of blanking, TRIP 34? 61 will be a NO, so sensing is initially in region A, 62 of (of FIG. 5). If it stays there until END ALERT 63, the microprocessor will DECREASE DAC OUTPUT—PER SPEC, 64. The rationale here is that no sensing took place, so lower the sense threshold (higher sensitivity).

If TRIP 34? 61 is a YES, the next question the system asks is does it DETECT NOISE? 65. Noise criteria can be defined in many different ways, but the most common is that if comparator 34 makes more than N-transitions within a specified time interval, the detected signal is classified noise. In such a case, NOISE FLAG 66 goes high for the balance of the pacer cycle (it gets reset at the next To). In the presence of noise, it is desired to automatically raise the sense threshold, in the hope that the cardiac signal will be detected "above the noise." For the system of FIG. 6 two algorithms are provided for increasing the DAC output, depending on whether the other comparator, TRIP 32? 67 is YES or NO. Following the NO path, we see that END ALERT? 68 times out while continuing to ask TRIP 32? 67. If the NO answer persists until END ALERT? 68 times out, the system enters INCREASE DAC OUTPUT—STEP A 69. On the other hand, if TRIP 32? 67 becomes a YES during the balance of the alert interval, the system goes into END ALERT? 70, which is "latched" until END ALERT? 70 times out. Since both comparators were tripped in this noise condition, INCREASE DAC OUTPUT—STEP B 71 provides a larger step size than step A. A simpler system can also be designed in which comparator 32 is not sensed and noise rate produces only one step size increase.

Because the blank interval is much shorter than the refractory interval, the noise state can be detected only in the post-blank/pre-alert interval. If noise somehow starts during the alert interval, it must begin by tripping comparator 34. As soon as that happens once, the system's pacing function zips through blocks 54, 56 and 57, to 50; ending as a valid cardiac signal; it inhibited output. However, this action initiates a new pacer cycle, and a new refractory interval. Therefore, immediately after the next blanking interval, the system reapplies the noise criteria in an uninterrupted manner. At worst, the patient missed one pacer pulse.

If DETECT NOISE? 65 and TRIP 32? 72 are both NO, the system is in region B, 73 (FIG. 5), as indicated. While in this state, END ALERT? 74=No, continues to ask if TRIP 32? 72 took place. If END ALERT 74 times out with the system still in region B (73), the sensitivity is appropriate, and the cycle ends with DAC OUTPUT UNCHANGED, 75.

If both comparators 32 and 34 tripped and the system has not detected noise, it is in region C, 76. There is a timing subtlety involved here in that the sense amplifier is relatively narrow-banded. Therefore, it introduces significant slew-rate limiting. As a result, even large cardiac signals will not trip 34 and 32 at the same time. Thus, if SLEW DELAY was not in block 57, a pacer pulse would have been issued as soon as TRIP 34? 54 became a YES, and a new pacer cycle would have commenced. Thus, the ensuing blank gate would have prevented TRIP 32 (72) from going to YES. SLEW DELAY 57 gives comparator 32 the time it needs to respond, it if is going to. Once this happens, the system latches END ALERT? 77 until it times out. When it does, the system INCREASES DAC OUTPUT—STEP C, in an attempt to get sensing back into region B, 73.

There are a few other housekeeping chores which are left to the microprocessor to handle. For example, in sampling blocks 64, 69, 71, 75 and 78, it must assign priorities. Clearly, the mutually exclusive noise rate responses 69 or 71 will be given top priority. Thus, if mutually inclusive 71 and 78 are both latched high, 71 will be implemented.

It can be seen that an automatic sensitivity control has been provided for cardiac pacers in which there can be a large number of sensitivity levels and in which only a single fixed gain amplifier needs to be used with each channel. There is no need to vary amplifier gain but instead two systems have been presented (including the "criss-cross" configuration) in which voltage levels at the inputs to a pair of voltage comparators are programmed for optimal responses to sensed cardiac conditions under the direct software control of the digital to analog converter.

Although a pair of illustrative embodiments of the invention have been shown and described, it is to be understood that various modifications and substitutions may be made by those skilled in the art without departing from the novel spirit, scope and intention of the present invention.

What is claimed is:

1. A cardiac pacer including a pulse generator for providing pacing pulses and an electrical lead for connection to a chamber of the heart, which comprises:
   a sensing amplifier for sensing a cardiac waveform, said sensing amplifier having a fixed gain;
   means for connecting said electrical lead to said fixed gain sensing amplifier;
   a pair of voltage comparators for receiving the same polarity of the cardiac waveform;
   means for coupling the output of said sensing amplifier to each of said voltage comparators so that both of said voltage comparators will receive the same polarity of the cardiac waveform;
one of said voltage comparators having a slightly lower threshold and thus a slightly higher sensitivity than the other voltage comparator; and
means for adjusting the thresholds of the respective voltage comparators so that one voltage comparator will sense said cardiac waveform that has been amplified by said sensing amplifier while said other voltage comparator will not sense said cardiac waveform that has been amplified by said sensing amplifier, said adjusting means including feedback means coupled to the outputs of each of said voltage comparators.

2. A cardiac pacer as described in claim 1, said coupling means comprising a circuit element having an output that is the absolute value of its input.

3. A cardiac pacer as described in claim 2, said circuit element comprising a precision signal rectifier.

4. A cardiac pacer as described in claim 1, said voltage comparators each comprising an analog comparator having a positive input and a negative input.

5. A cardiac pacer as described in claim 4, said coupling means comprising a precision signal rectifier having an output that is the absolute value of its input, said rectifier output being coupled to said positive input of both voltage comparators.

6. A cardiac pacer as described in claim 4, said adjusting means including means for providing sensing threshold levels to said negative inputs so that (a) if neither voltage comparators sense the cardiac waveform the thresholds of both voltage comparators are decreased, (b) if said one voltage comparator senses the cardiac waveform but said other voltage comparator does not sense the cardiac waveform, then the threshold levels are unchanged, and (c) if both voltage comparators sense the cardiac waveform then the thresholds of both voltage comparators are increased.

7. A cardiac pacer as described in claim 6, said adjusting means comprising a digital to analog converter; means for providing digital signals to said digital to analog converter; a resistive scaling circuit coupled to the output of the digital to analog converter and to the negative inputs of the voltage comparators for providing a different voltage to each of said negative inputs.

8. A cardiac pacer as described in claim 7, said means for providing digital signals to said digital to analog converter comprising a microprocessor; and means coupling the outputs of said voltage comparators to an input of said microprocessor.

9. A cardiac pacer as described in claim 1, in which the threshold of said other voltage comparator is about 25 percent greater than the threshold of said one voltage comparator.

10. A cardiac pacer as described in claim 1, wherein said voltage comparators are identical in internal construction to each other.

11. A cardiac pacer as described in claim 1, said adjusting means comprising means for providing signals to said voltage comparators so that (a) if neither voltage comparators sense the cardiac waveform the thresholds of both voltage comparators are decreased, (b) if said one voltage comparator senses the cardiac waveform but said other voltage comparator does not sense the cardiac waveform, the signals are unchanged, and (c) if both voltage comparators sense the cardiac waveform the thresholds of both voltage comparators are increased.

12. A cardiac pacer including a pulse generator for providing pacing pulses and an electrical lead for connection to a chamber of the heart, which comprises:
a sensing amplifier for sensing a cardiac waveform;
means for connecting said electrical lead to said sensing amplifier;
a first voltage comparator for receiving a selected polarity of the cardiac waveform;
a second voltage comparator for receiving said selected polarity of the cardiac waveform;
said second voltage comparator having a slightly lower threshold and thus a slightly higher sensitivity than said first voltage comparator;
means for coupling the output of said sensing amplifier to said first and second voltage comparators so that said first and second voltage comparators will receive the same polarity of the cardiac waveform;
feedback means coupld to the outputs of each of said voltage comparators for adjusting the thresholds of said first and second voltage comparators so that (a) if neither of said voltage comparators sense the cardiac waveform the thresholds of both voltage comparators are decreased, (b) if said second voltage comparator senses the cardiac waveform but said first voltage comparator does not sense the cardiac waveform, no further adjustment is made, and (c) if both said first and second voltage comparators sense the cardiac waveform the thresholds of both voltage comparators are increased;
said adjusting means including feedback means coupled to the outputs of each of said voltage comparators.

13. A cardiac pacer as described in claim 12, in which said sensing amplifier has a fixed gain and said voltage comparators are internally identical to each other and are each analog comparators having a positive input and a negative input.

14. A cardiac pacer as described in claim 13, said adjusting means comprising means for providing sensing threshold levels to said negative inputs, said adjusting means comprising a digital to analog converter, a microprocessor for providing digital signals to said digital to analog converter, and a resistive scaling circuit coupled to the output of the digital to analog converter and to the negative inputs of the voltage comparators for providing a different voltage to each of said negative inputs; and means coupling the outputs of said voltage comparators to an input of said microprocessor.

15. A cardiac pacer including a pulse generator for providing pacing pulses and an electrical lead for connection to a chamber of the heart, which comprises:
a fixed gain, tuned sensing amplifier for sensing a cardiac waveform;
means for connecting said electrical lead to said fixed gain, tuned sensing amplifier;
a pair of voltage comparators for receiving the same polarity of the cardiac waveform, said voltage comparators being internally identical to each other and each comprising an analog comparator having a positive input and a negative input;
means for coupling the output of said sensing amplifier to each of said voltage comparators so that both of said voltage comparators will receive the same polarity of the cardiac waveform;
said coupling means comprising a precision signal rectifier having an output that is the absolute value of its input, said rectifier output being coupled to said positive input of both voltage comparators;

one of said voltage comparators having a slightly lower threshold and thus a slightly higher sensitivity than the other voltage comparator;

feedback means coupled to the outputs of each of said voltage comparators for adjusting the thresholds of the respective voltage comparators, said feedback means including means for providing sensing threshold levels to said negative inputs so that (a) if neither voltage comparators sense the cardiac waveform the thresholds of both voltage comparators are decreased, (b) if said one voltage comparator senses the cardiac waveform but said other voltage comparator does not sense the cardiac waveform, the threshold levels are unchanged, and (c) if both voltage comparators sense the cardiac waveform the thresholds of both voltage comparators are increased;

said feedback means comprising a digital to analog converter;

means for providing digital signals to said digital to analog converter;

a resistive scaling circuit coupled to the output of the digital to analog converter and to the negative inputs of the voltage comparators for providing a different voltage to each of said negative inputs;

said means for providing digital signals to said digital to analog converter comprising a microprocessor; and said feedback means coupling the outputs of said voltage comparators to an input of said microprocessor.

* * * * *